United States Patent
Benestad

(10) Patent No.: US 7,032,455 B2
(45) Date of Patent: Apr. 25, 2006

(54) CAPACITIVE SENSOR DEVICE

(76) Inventor: Harald Benestad, Røahagen 34, N-0754 Oslo (NO)

( * ) Notice: Subject to any disclaimer, the term of this patent is extended or adjusted under 35 U.S.C. 154(b) by 101 days.

(21) Appl. No.: 10/482,958

(22) PCT Filed: Jul. 9, 2002

(86) PCT No.: PCT/NO02/00252

§ 371 (c)(1),
(2), (4) Date: Jan. 8, 2004

(87) PCT Pub. No.: WO03/006978

PCT Pub. Date: Jan. 23, 2003

(65) Prior Publication Data

US 2004/0163480 A1 Aug. 26, 2004

(30) Foreign Application Priority Data

Jul. 10, 2001 (NO) .......................................... 20013411

(51) Int. Cl.
*G01F 1/56* (2006.01)

(52) U.S. Cl. .......................... 73/706; 73/718; 73/204.22
(58) Field of Classification Search .................. 73/706, 73/718, 724, 861, 204.22; 361/283.4
See application file for complete search history.

(56) References Cited

U.S. PATENT DOCUMENTS 4,587,840 A    5/1986   Dobler et al.
4,994,781 A  * 2/1991   Sahagen ....................... 338/47
5,824,909 A  * 10/1998  Kathan et al. ................. 73/706
6,363,790 B1 * 4/2002   Flogel et al. .................. 73/708
6,422,085 B1 * 7/2002   Hegner et al. ................. 73/706

FOREIGN PATENT DOCUMENTS

| DE | 3231206 A1 | 2/1984 |
|---|---|---|
| EP | 0038551 A1 | 10/1981 |
| EP | 0564428 A1 | 10/1993 |
| EP | 0701110 A2 | 3/1996 |
| WO | WO/9845672 A1 | 10/1998 |
| WO | WO 00/25102 A1 | 5/2000 |

OTHER PUBLICATIONS

PCT International Search Report (International Application No. PCT/NO02/00252) dated Oct. 23, 2002.

* cited by examiner

*Primary Examiner*—William Oen
*Assistant Examiner*—Andre Allen
(74) *Attorney, Agent, or Firm*—Rodman & Rodman

(57) ABSTRACT

A capacitive sensor device for measuring properties of a medium to be measured when this medium surrounds and flows past the sensor. The sensor has a housing of metal, an opening in the housing transverse to the flow of said medium to be measured which is adapted to house at least one capacitive electrode, and where the electrode(s) of the sensor is/are electrically insulated from said medium to be measured by means of a glass ceramic material that is arranged to be flush with the outer surface of the sensor.

19 Claims, 4 Drawing Sheets

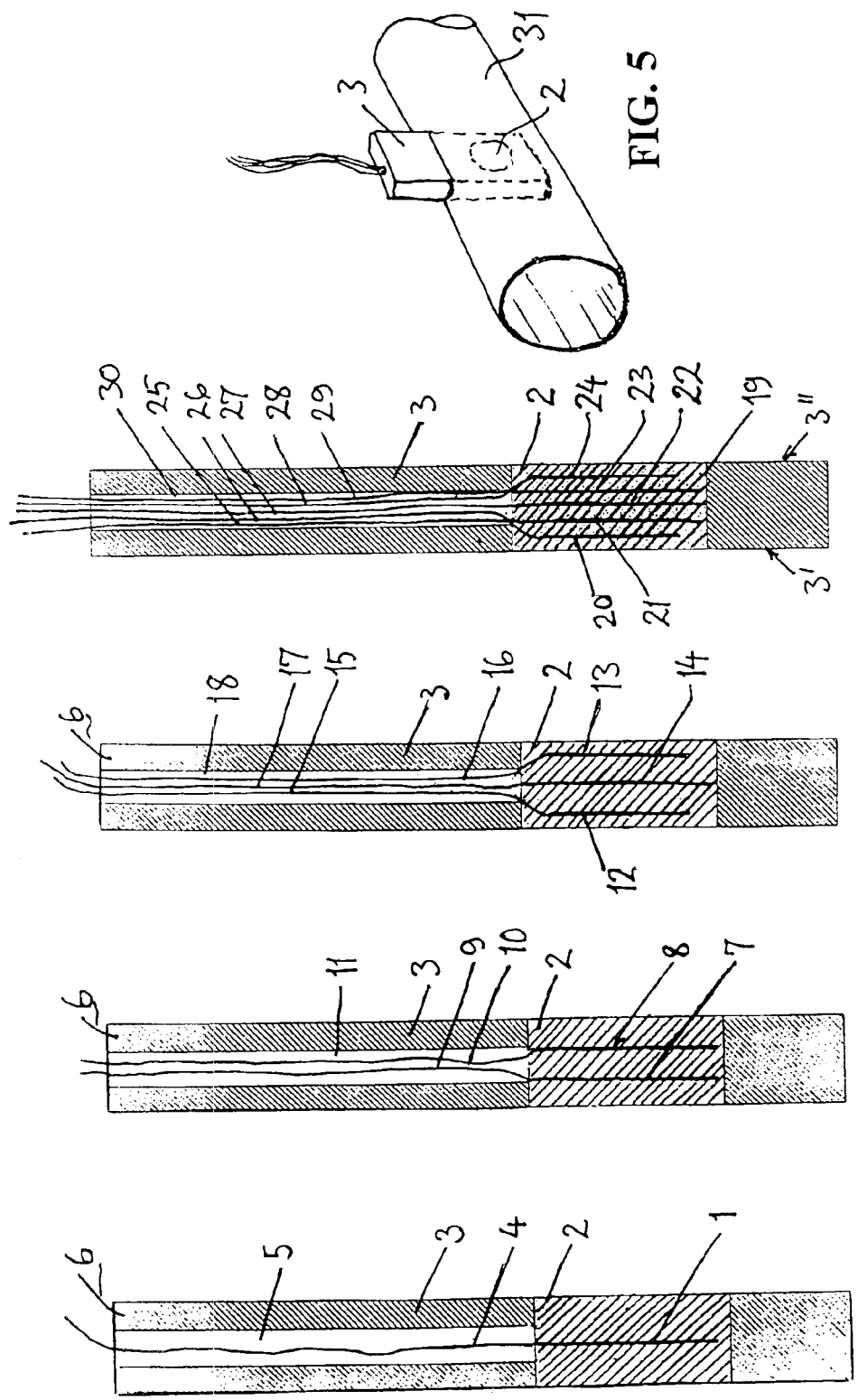

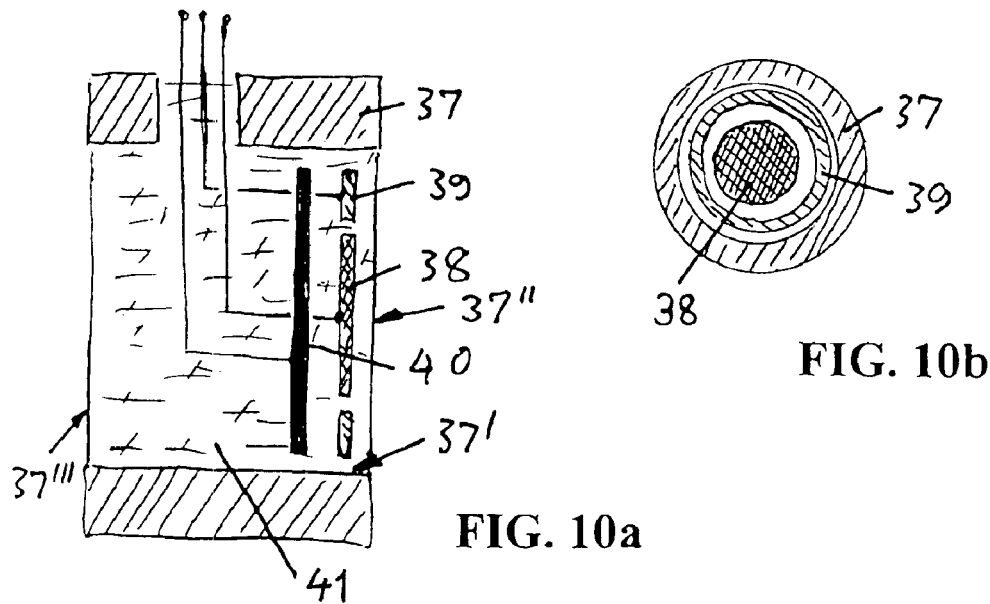
FIG. 10a
FIG. 10b
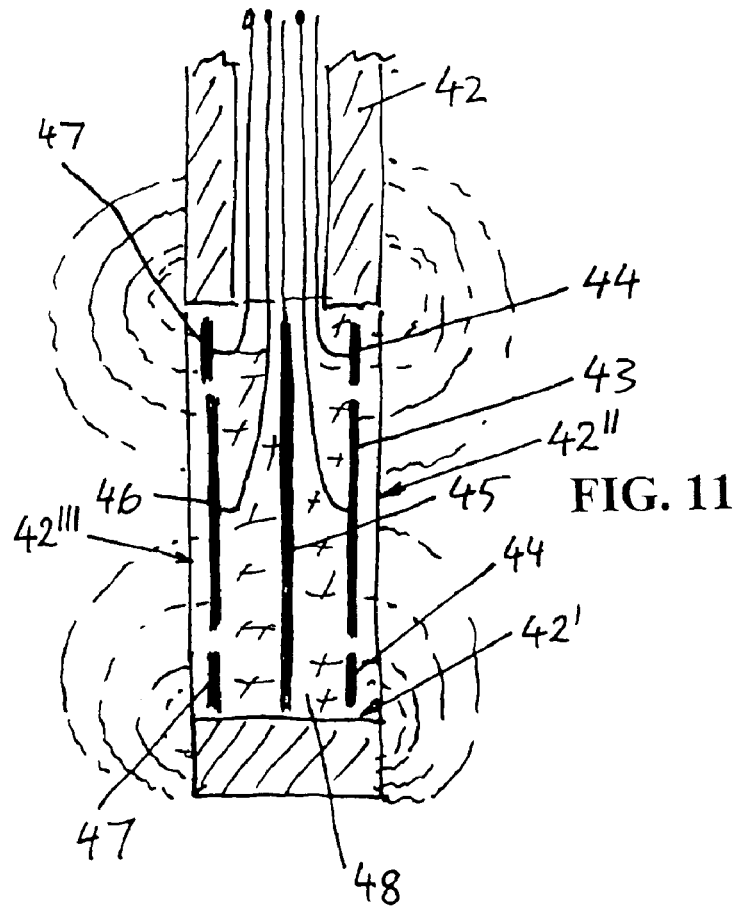
FIG. 11

CAPACITIVE SENSOR DEVICE

The present invention relates to a capacitive sensor device for measuring properties of a medium to be measured when this medium surrounds and flows past the sensor, where the sensor has a housing of metal, and where the electrode(s) of the sensor is/are electrically insulated from said medium to be measured by means of a glass ceramic material that is arranged to be flush with the outer surface of the sensor.

The prior art includes a number of devices for capacitive measurement of properties of a medium to be measured which flows, for example, through a pipeline. However, there has long been a desire to provide a capacitive sensor that is robust, resistant to any corrosive medium to be measured, and in addition provides increased sensitivity in comparison with the known solutions.

Accordingly, the present invention is characterised in that an opening in the housing transverse to the flow of the medium to be measured is designed to house at least one capacitive electrode, and that the electrode(s) of the sensor is/are electrically insulated from said medium to be measured by means of said glass ceramic material that is arranged to be flush with the opposite faces of the sensor housing.

In an alternative embodiment, the sensor is characterised in that an opening in the housing transverse to the flow of said medium to be measured is designed to house at least two electrodes which are electrically insulated from each other at a fixed distance and from said medium to be measured by means of said glass ceramic material that is arranged to be flush with the opposite faces of the sensor housing.

According to another embodiment in which there are at least two electrodes, the electrodes of the sensor, when viewed from one face of the sensor housing to the opposite face, consist of a first capacitive sensor electrode, a common reference electrode that is in galvanic contact with the sensor housing, and a second capacitive sensor electrode.

In an alternative embodiment in which the sensor has at least two electrodes, the electrodes of the sensor, when viewed from one face of the sensor housing to the opposite face, consist of a first capacitive sensor electrode, a first counter-phase or shield electrode, a common reference electrode that is in galvanic contact with the sensor housing, a second counter-phase or shield electrode and a second capacitive sensor electrode.

In another alternative embodiment, the electrodes of the sensor, when viewed from one face of the sensor housing to the opposite face, consist of a) a capacitive sensor electrode that is surrounded in the same plane by a ring-shaped counter-phase or shield electrode, and b) a common reference electrode.

According to yet another embodiment, the electrodes of the sensor, when viewed from one face of the sensor housing to the opposite face, consist of a) a first capacitive sensor electrode that is surrounded in the same plane by a first ring-shaped counter-phase or shield electrode, b) a common reference electrode, and c) a second capacitive sensor electrode that is surrounded in the same plane by a second ring-shaped counter-phase or shield electrode, the reference electrode being common to the electrodes in both point a) and point b).

It is an advantage if the counter-phase or shield electrodes are made in the form of rings having an internal diameter smaller than the diameter of the capacitive electrode and an outer diameter greater than the diameter of the capacitive electrode.

It would also be advantageous to allow the electrodes of the sensor to be disc-shaped with a conical or polygonal contour.

When the electrodes of the sensor comprise counter-phase or shield electrodes, these electrodes will preferably have a larger surface area than the capacitive sensor electrodes.

Furthermore, it would be advantageous if the sensor housing, seen in cross-section, were given an aerodynamic form.

Said medium to be measured may, for example, consist of one fluid or several fluids in a mixture. The term "fluid" in this context is to be understood in its widest sense, and includes, e.g., liquid, gas, a mixture of liquid and gas (also including air), liquid and/or gas containing particles (e.g., sand), or consist of, e.g., powder or a powder composition, optionally in connection with a fluid, as for instance air.

The invention will now be explained in more detail with reference to the attached figures.

FIG. 1–FIG. 4 show four alternative embodiments of the device according to the invention.

FIG. 5 shows a preferred use of the device in connection with, for example, a pipeline.

FIGS. 10a and 10b show a fifth embodiment of the device according to the invention.

FIG. 11 shows a sixth embodiment of the device according to the invention.

Figure 6:
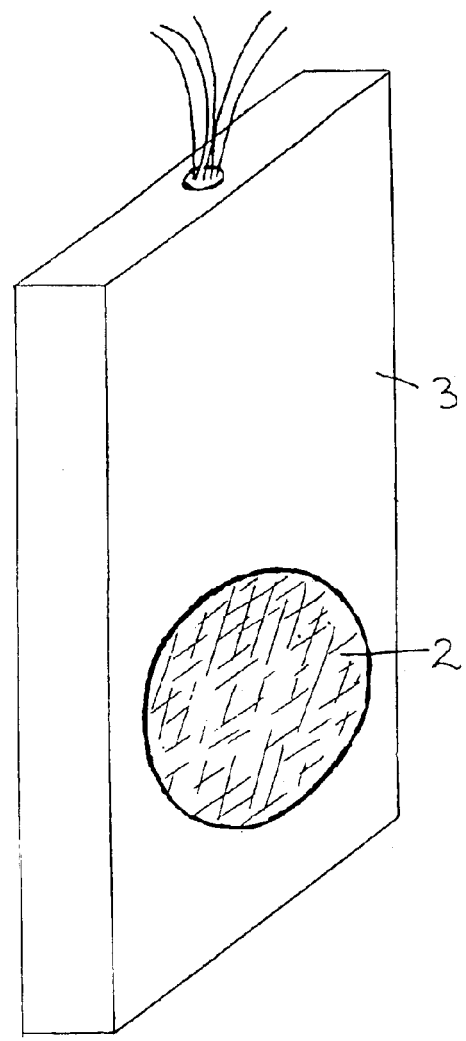
FIG. 6 is a perspective view of the device.

In its simplest form, the device may consist of a single electrode 1 which is embedded in a glass ceramic material 2 in the sensor housing 3. A wire connection 4 leads to the outside of the sensor housing 3 via a duct 5. The sensor housing has a wire connection 6. Thus, the sensor housing 3 will in this case act as a reference electrode.

In the embodiment shown in FIG. 2 there are two capacitive electrodes 7, 8 which are embedded in a glass ceramic material 2, and wires 9, 10 run from the electrodes 7, 8 via a wire duct 11 to the outside of the housing 3. In this case too, the housing 3 will form a reference or counter-electrode to the electrodes 7, 8.

In the embodiment shown in FIG. 3 two capacitive electrodes 12, 13 are provided, and between them a reference electrode 14 which preferably, but not necessarily, is on the same potential as the housing 3. Here too, the electrodes 12–14 are embedded in a glass ceramic material 2 in an opening in the housing 3.

The electrodes 12–14 are connected to the outside of the housing 3 via respective wires 15, 16, 17, which run through a duct 18 in the housing 3.

In the fourth embodiment shown in FIG. 4, the sensor has a total of five electrodes placed in the opening 19 in the housing 3. Also in this case, all the electrodes are embedded in a glass ceramic material, and here too the glass ceramic material 2 will be flush with opposite faces 3', 3" of the housing 3. When viewed from left to right in FIG. 4, i.e., from the face 3' to the face 3", there is a first capacitive sensor electrode 20, a first counter-phase or shield electrode (so-called "Guard" electrode) 21, a common reference electrode 22, a second counter-phase or shield electrode 23 and a second capacitive sensor electrode 24. The counter-phase or shield electrodes 21, 24 will in effect create a form of screen or reference platform for the capacitive electrodes, and the housing 3 will form a counter-electrode. The respective electrodes 20–24 are connected to the outside of the sensor housing 3 via respective wires 25–29 which run through a duct 30 in the housing 3.

In FIG. 6 the sensor is shown in perspective, as it will in fact look for all the embodiments shown in FIGS. 1–4. In FIG. 5 the sensor has been placed purely schematically in a pipeline, and where the opposite faces 3', 3" are essentially parallel to the flow direction of the medium flowing though the pipeline 31.

Figure 7:
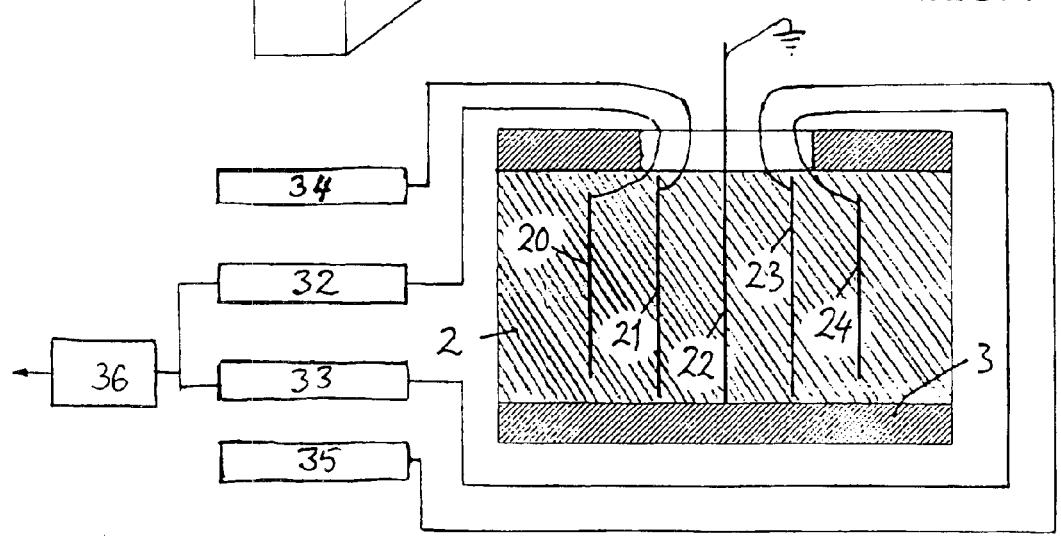
FIG. 7 shows a preferred, but not necessarily limiting circuit diagram for electrical equipment connected to the electrodes in connection with one of the embodiments.

FIG. 7 shows a typical, but not necessarily limiting exemplary embodiment of the circuits which could control the electrodes 20–24 when there is a total of five electrodes. The reference numerals 32 and 33 indicate respectively a first and a second oscillator which are connected to a first and second capacitive electrode 20, 24. The reference numerals 34 and 35 indicate counter-phase/shield driver electronics to drive the electrodes 21, 23 in opposite phase to the electrodes 20, 24 so as to obtain an efficient screening and create a platform or base for the electrodes 20 and 24. This also allows the detection field to be pushed further out into the medium. Like the housing 3, the electrode 22 is connected to earth. The reference numeral 36 indicates a signal circuit connected to the oscillators 32 and 33 to detect signal variations and thus provide an expression of properties of the medium flowing past the sensor.

The fact that the sensor is actually two-sided means that increased sensitivity is obtained in relation to what is previously known in connection with capacitive sensors which traditionally are placed in, for example, the pipeline wall.

The electrodes of the sensor are preferably disc-shaped, and may optionally be given a conical or polygonal contour, preferably matching the shape of the opening 19 in the housing 3. It would be advantageous, with the object of causing minimum turbulence, to give the sensor housing, insofar as possible, an aerodynamic form. This is indicated to some extent in FIG. 5. In an alternative embodiment, the electrodes 21, 23 may be ring-shaped and have an inner diameter smaller than the diameter of the respective, adjacent capacitive electrode, and an outer diameter greater than the diameter of the capacitive electrode.

Figure 8:
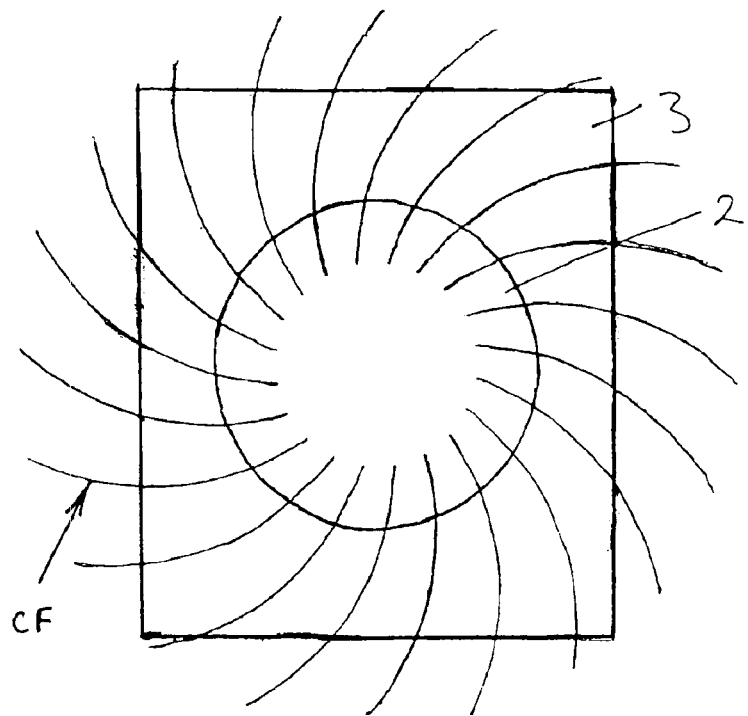
FIGS. 8 and 9 show, as examples, capacitive fields that are produced in connection with the device.
Figure 9:
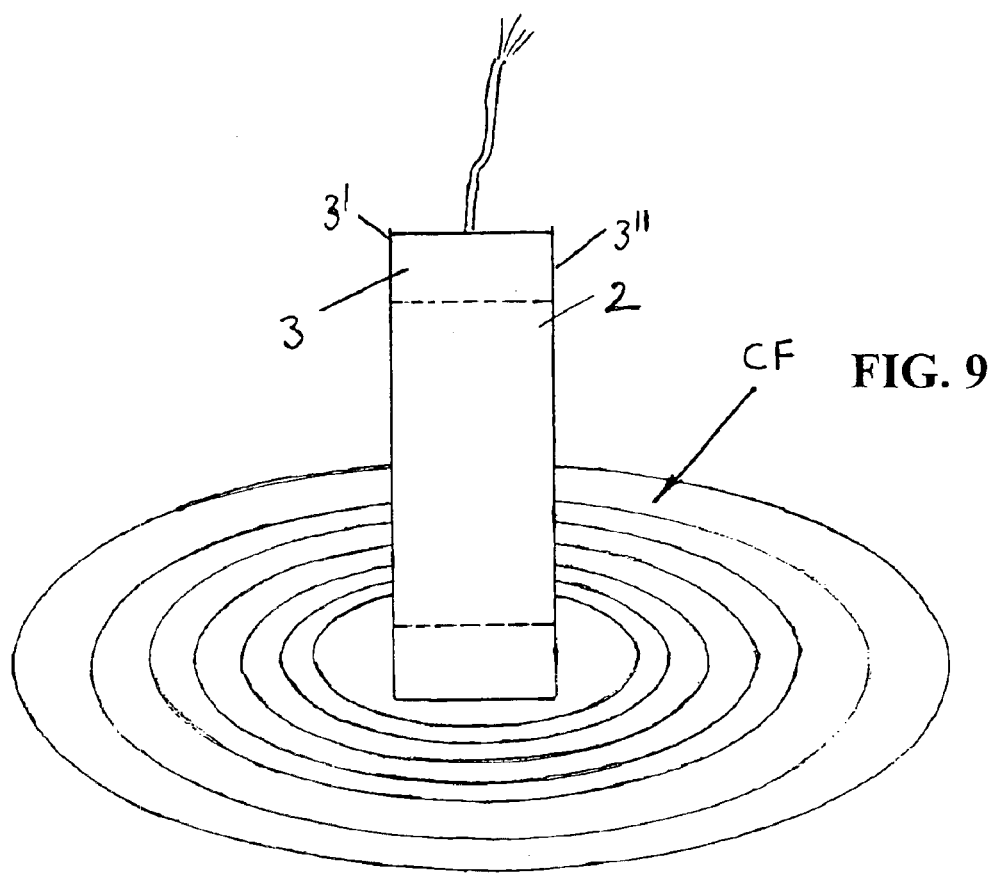

For the sake of simplicity, the electrodes have not been included in FIG. 8 and FIG. 9, but it will be seen that, in particular in the embodiment shown in FIG. 4, a capacitive field CF is obtained which extends from one side 3' of the sensor housing to the opposite side 3", as indicated in FIG. 9 and also indicated to a certain extent in FIG. 8.

It is important to note that when the glass ceramic material 2 is used, the distance between the electrodes, if there are two or more electrodes, will be fixed and will therefore be independent of pressure and temperature.

The electrodes 21 and 23, as shown in connection with FIG. 4 and FIG. 7, prevent the sensor electrodes 20 and 24 from being affected by each other and will also provide a fixed capacity that is small is relation to the measurement capacity provided by the sensor electrodes 20 and 24. The electrodes 21 and 23 can expediently be connected to an extra screen in a measuring cable (not shown) and also to associated electronic equipment 34, 35, as shown in FIG. 7.

As indicated in FIG. 9, the measuring field will extend from one sensor electrode through the glass ceramic material, then through the material to be measured, and then through the glass ceramic material to the other sensor electrode.

As shown in FIGS. 4 and 7, the counter-phase electrodes can preferably have a greater diameter than the sensor electrodes 20, 24 and will thus cause the measuring field to reach further into the medium to be measured than would be the case if such electrodes 21, 23 were not used.

If only one electrode is used, as shown in FIG. 1, without the use of the electrodes 21, 23 and 22, the measuring field will be between the sensor housing that is exposed to the medium to be measured and the sensor electrode 1 that lies insulated in the glass ceramic material 2. By using a two-sided electrode of this kind, where both sides are exposed to the medium to be measured, the capacity provided by the sensor will in fact be great, with a measuring field that is contiguous with the sensor housing 3.

In the solution that can be seen from either FIG. 2 or FIG. 3, where there are two sensor electrodes 7, 8; 12, 13, these electrodes will, as shown, also both lie insulated in the glass ceramic material 2, and the field will extend between both sides of the sensor, as shown and described in connection with FIGS. 8 and 9.

FIGS. 10a and 10b show an embodiment which differs slightly from what has been shown in the preceding figures. The sensor housing is indicated by the reference numeral 37 in these figures, and has a through opening 37' in which the sensor electrodes 38, 39 and 40 are placed, and where the opening is filled with glass ceramic material 41 which surrounds and holds the electrodes apart at a fixed distance. The electrodes of the sensor, when viewed from one face 37" of the sensor housing to the opposite face 37''', consist of a capacitive sensor electrode 38 that is surrounded in the same plane by a ring-shaped counter-phase or shield electrode 39. These two electrodes have a common reference electrode 40. The actual housing may have an earth potential or a potential in common with the reference electrode. The counter-phase or shield electrode, a so-called "Guard" electrode, helps to ensure that the main field from the capacitive electrode is pushed further out into the medium to be measured, whereby the sensitivity of the sensor is also increased.

An alternative embodiment of that shown in FIG. 10 can be seen in FIG. 11. In this figure, the sensor housing is indicated by the reference numeral 42 and has a through opening 42', in which the sensor electrodes 43–47 are placed, and where the opening is filled with a glass ceramic material 48 which surrounds and holds the electrodes apart at a fixed distance. The electrodes of the sensor, when viewed from one face 42" of the sensor housing to the opposite face 42''', consist of a capacitive sensor electrode 43 which is surrounded in the same plane by a ring-shaped counter-phase or shield electrode 44. These two electrodes have a common reference electrode 45. A second capacitive sensor electrode 46 that is surrounded in the same plane by a second ring-shaped counter-phase or shield electrode 47 is placed at a distance from the reference electrode 45, but the reference electrode 45 will be common to all the electrodes 43, 44 and 46, 47. The actual housing 42 may have an earth potential or a potential in common with the reference electrode. Here too, the counter-phase or shield electrodes 44, 47, so-called "Guard" electrodes, will help to ensure that the main field from the respective, adjacent capacitive electrode 43, respectively 46, is pushed further out into the medium to be measured, thereby also increasing the sensitivity of the sensor. The advantage of the embodiment shown in FIG. 11 is that the sensor in this case, compared with the embodiment shown in FIG. 10, has considerably greater sensitivity because of the possibility of two-sided detection.

What is claimed is:

1. A capacitive sensor device for measuring properties of a medium to be measured when this medium surrounds and flows past the sensor, where the sensor has a housing (3; 37;

42) of metal, with an opening (19) in the housing designed to accommodate one or more electrode(s) (1; 7, 8; 12–14; 20–24; 38–40; 43–47), said electrode(s) being electrically insulated from said medium to be measured by means of a glass ceramic material (2; 41; 48) that is arranged to be flush with the outer surface of the sensor housing (3), characterised in that said opening (19; 37'; 42') in the housing relative to the flow of said medium to be measured is located transversely thereof between two opposite faces (3', 3"; 37', 37"; 42', 42") of the sensor housing.

2. A capacitive sensor device according to claim 1, characterised in that the opening (19; 37'; 42') in the sensor housing (3; 37; 42) is capable of housing at least one capacitive electrode (1; 7,8; 12–14; 20–24; 38–40; 43–47).

3. A capacitive sensor device according to claim 1, characterised in that the opening (19; 37'; 42') in the sensor housing (3; 37; 42) is capable of housing at least two electrodes (7, 8; 12–14; 20–24; 38–40; 43–47) which are electrically insulated from each other by a fixed mutual spacing.

4. A capacitive sensor device according to claim 2, characterised in that said at least one electrode is electrically insulated from said housing by means of said glass ceramic material (2; 41; 48).

5. A capacitive sensor device according to claim 3, characterised in that said at least two electrodes are electrically insulated from each other and from said housing by means of said glass ceramic material (2; 41; 48).

6. A device as disclosed in claim 3, characterised in that the sensor electrodes, when viewed from one face of the sensor housing to the opposite face, consist of a first capacitive sensor electrode (12), a common reference electrode (14), and a second capacitive sensor electrode (13).

7. A device as disclosed in claim 3, characterised in that the sensor electrodes, when viewed from one face of the sensor housing to the opposite face, consist of a first capacitive sensor electrode (20), a first counter-phase or shield electrode (21), a common reference electrode (22), a second counter-phase or shield electrode (23), and a second capacitive sensor electrode (24).

8. A device as disclosed in claim 3, characterised in that the sensor electrodes, when viewed from one face of the sensor housing to the opposite face, consist of a) a capacitive sensor electrode (38) that is surrounded in the same plane by a ring-shaped counter-phase or shield electrode (39), and b) a common reference electrode (40).

9. A device as disclosed in claim 3, characterised in that the sensor electrodes, when viewed from one face of the sensor housing to the opposite face, consist of a) a first capacitive sensor electrode (43) that is surrounded in the same plane by a first ring-shaped counter-phase or shield electrode (44), b) a common reference electrode (45), and c) a second capacitive sensor electrode (46) that is surrounded in the same plane by a second ring-shaped opposite-phase or shield electrode (47), the reference electrode (45) being common to the first and second capacitive sensor electrodes and located midway therebetween.

10. A device as disclosed in claim 1, characterised in the sensor electrode(s) being disc-shaped with a conical or polygonal contour.

11. A device as disclosed in claim 6, characterised in the counter-phase or shield electrode(s) having a larger surface area than the capacitive sensor electrodes.

12. A device as disclosed in claim 7, characterised in that the counter-phase or shield electrodes are made in the form of rings having an internal diameter smaller than the diameter of the capacitive electrode and an external diameter greater than the diameter of the capacitive electrode.

13. A device as disclosed in claim 1, characterised in that the sensor housing, seen in cross-section, has an aerodynamic shape.

14. A device as disclosed in claim 1, characterised in that said medium to be measured consists of a fluid or several fluids in a mixture, e.g., liquid, gas, a mixture of liquid and gas (also including air), liquid and/or gas containing particles (e.g., sand).

15. A device as disclosed in claim 1, characterised in that said medium to be measured consists of powder or a powder composition, optionally in connection with a fluid, e.g., air.

16. A device as disclosed in claim 15, characterized in that said medium is flowing together with a fluid, e.g., air.

17. A device as disclosed in claim 1, characterized in that said sensor housing (3) forms a reference electrode.

18. A device as disclosed in claim 1, characterized in that said sensor housing (3) forms a reference electrode or counter electrode.

19. A device according to claim 6, characterised in that said common reference electrode (14; 22; 40; 45) is connectable to a same potential as that of said housing.

* * * * *